(12) United States Patent
Appling et al.

(10) Patent No.: US 10,918,833 B2
(45) Date of Patent: Feb. 16, 2021

(54) MODULAR HANDLE ASSEMBLY FOR A STEERABLE CATHETER

(71) Applicant: FREUDENBERG MEDICAL, LLC, Carpinteria, CA (US)

(72) Inventors: Anthony Appling, Crestwood, KY (US); Greg Furnish, Louisville, KY (US); Ben Morris, Jeffersonville, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 352 days.

(21) Appl. No.: 16/142,801

(22) Filed: Sep. 26, 2018

(65) Prior Publication Data
US 2020/0094020 A1    Mar. 26, 2020

(51) Int. Cl.
*A61M 25/01* (2006.01)

(52) U.S. Cl.
CPC .... *A61M 25/0147* (2013.01); *A61M 25/0136* (2013.01); *A61M 2025/015* (2013.01); *A61M 2025/0175* (2013.01)

(58) Field of Classification Search
CPC .... A61M 2025/015; A61M 2025/0175; A61M 25/0136; A61M 25/0147; A61B 1/008; A61B 1/2034; A61B 1/0052; A61B 1/0057

See application file for complete search history.

(56) References Cited

U.S. PATENT DOCUMENTS

| | | | |
|---|---|---|---|
| 5,358,478 A | 10/1994 | Thompson et al. | |
| 5,456,664 A * | 10/1995 | Heinzelman | A61M 25/0136 600/585 |
| 6,263,224 B1 * | 7/2001 | West | A61M 25/0136 600/373 |
| 6,652,506 B2 | 11/2003 | Bowe et al. | |
| 7,465,288 B2 | 12/2008 | Dudney et al. | |
| 7,682,358 B2 | 3/2010 | Gullickson et al. | |
| 8,323,239 B2 | 12/2012 | Bednarek et al. | |
| 8,617,087 B2 | 12/2013 | Schultz | |
| 8,777,929 B2 | 7/2014 | Schneider et al. | |
| 9,132,258 B2 | 9/2015 | Bednarek et al. | |
| 9,174,024 B1 | 11/2015 | Romoscanu et al. | |
| 9,220,868 B2 | 12/2015 | Schultz | |
| 9,833,595 B2 * | 12/2017 | Gonzalez | A61B 1/0052 |
| 9,861,788 B2 | 1/2018 | Yu et al. | |
| 2009/0105645 A1 * | 4/2009 | Kidd | A61M 25/0133 604/108 |
| 2016/0348769 A1 * | 12/2016 | Siegal | A61B 17/00234 |

\* cited by examiner

*Primary Examiner* — Quynh-Nhu H. Vu
(74) *Attorney, Agent, or Firm* — Dickinson Wright PLLC

(57) ABSTRACT

A modular handle assembly includes a dial rotatably connected to a handle and rotatable about a first rotary axis. A first gear arm extends from the dial and terminates at a first traction surface. A second gear arm is connected to the handle and rotatable about a second rotary axis that is parallel to the first rotary axis. The second gear arm terminates at a second gear tip that presents a second traction surface disposed against the first traction surface such that rotation of the dial in a first rotary direction effectuates rotation of the second gear arm in an opposite direction. A cam is coupled with at least one of the first and second gear tips and presents at least one deflection surface for deflecting a deflection wire during rotation of the dial to steer a distal end of a steerable catheter containing the deflection wire.

20 Claims, 6 Drawing Sheets

MODULAR HANDLE ASSEMBLY FOR A STEERABLE CATHETER

BACKGROUND OF THE INVENTION

1. Field of the Invention

The present invention relates to steerable catheters, and more particularly to a modular handle assembly for supporting and controlling a steerable catheter.

2. Description of the Prior Art

This section provides background information related to the present disclosure which is not necessarily prior art.

Catheters (i.e., catheters or sheaths) that have flexible tubular bodies with deflectable distal ends and control handles for controlling distal end deflection are used for many non-invasive medical producers. The distal portion of the catheter body is selectively deformed into a variety of curved configurations using an actuator on the control handle which remains outside the patient's body. The actuator is commonly internally linked to the distal portion of the catheter body by at least one deflection wire. Some catheter bodies employ a single deflection wire, which is pulled (i.e., placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

Although the prior art control handles are capable of controlling distal end deflection of catheter bodies, they have several drawbacks. For example, the prior art control handles are often excessively bulky and oftentimes expensive. Additionally, the prior art control handles often have a mechanical component that requires a significant effort to operate on the part of the user, and once a desired distal end deflection has been reached, the control handles typically require the operator to take a conscious step to maintain the catheter at the desired deflection. Further, the prior art control handles cannot be easily modified, and thus are only designed to work with a specific steerable catheter design.

Accordingly, there remains a need in the art for an improved control handle for use with a steerable catheter.

SUMMARY OF THE DISCLOSURE

This section provides a general summary of the disclosure and is not intended to be a comprehensive disclosure of its full scope, aspects, objectives, and/or all of its features.

A modular handle assembly for supporting and controlling a steerable catheter having at least one deflection wire includes a handle extending along a longitudinal axis for being positioned about a portion of the steerable catheter. A dial is rotatably connected to the handle and rotatable about a first rotary axis extending transverse to the longitudinal axis. A first gear arm extends radially relative to the first rotational axis from the dial and terminates at a first traction surface. A second gear arm is rotatably connected to the handle and is rotatable about a second rotary axis that extends in spaced and parallel relationship with the first rotary axis. The second gear arm extends radially relative to the second rotary axis and terminates at a second gear tip that presents a second traction surface disposed against the first traction surface such that rotation of the dial in a first rotary direction about the first rotary axis effectuates rotation of the second gear arm in an opposite direction about the second rotary axis. A cam is coupled with at least one of the first and second gear tips for corresponding movement of the cam during rotation of the dial. The cam presents at least one deflection surface for deflecting the at least one deflection wire extending across the at least one deflection surface during rotation of the dial to steer a distal end of the steerable catheter with the first and second gear tips.

Accordingly, the modular handle assembly has a unique arrangement of the dial, first and second gear arms and cam for effectuating movement of the at least one deflection wire. More particularly, the modular handle assembly allows the at least one deflection wire to advantageously be assembled taut and cam pushes outwardly on the at least one deflection wire to tension it during rotation of the dial. This action shortens the distance between a fixed termination point of the at least one deflection wire in the handle and the distal tip of the catheter where the at least one deflection wire is attached as compared to prior art steerable catheter handles which pull the deflection wires axially or wrap the wire around a drum to effectuate movement of the catheter. This allows controlled, short movements of the dial to effectuate movement of the distal end of the catheter.

Additionally, the modular handle assembly advantageously uses a novel dial arrangement while still providing users with a rotational movement during operation that is similar to conventional steerable catheter handles and thus familiar to current users.

Additionally, as will be explained in greater detail below, the subject modular handle assembly advantageously allows multiple deflection wires to be utilized, with all of the deflection wires terminating at a single point in the handle. This is contrary to conventional steerable catheter handles which have a respective termination point for each deflection wire.

Additionally, as will be explained in further detail below, the subject modular handle assembly advantageously does not require the use of deflection wires having a transition of a metal wire to a polymer fiber as is used with conventional steerable catheter handles because the subject modular handle assembly does not require the at least one deflection wire to be actively wound about a barrel or the like during bending of the distal end of the catheter.

Additionally, the subject modular handle assembly is simple to assemble during manufacturing and provides a compact arrangement of the working components which can easily be retrofitted into existing steerable catheter handles.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to a modular handle assembly 20 for supporting and controlling a steerable catheter 24.

Figure 1:
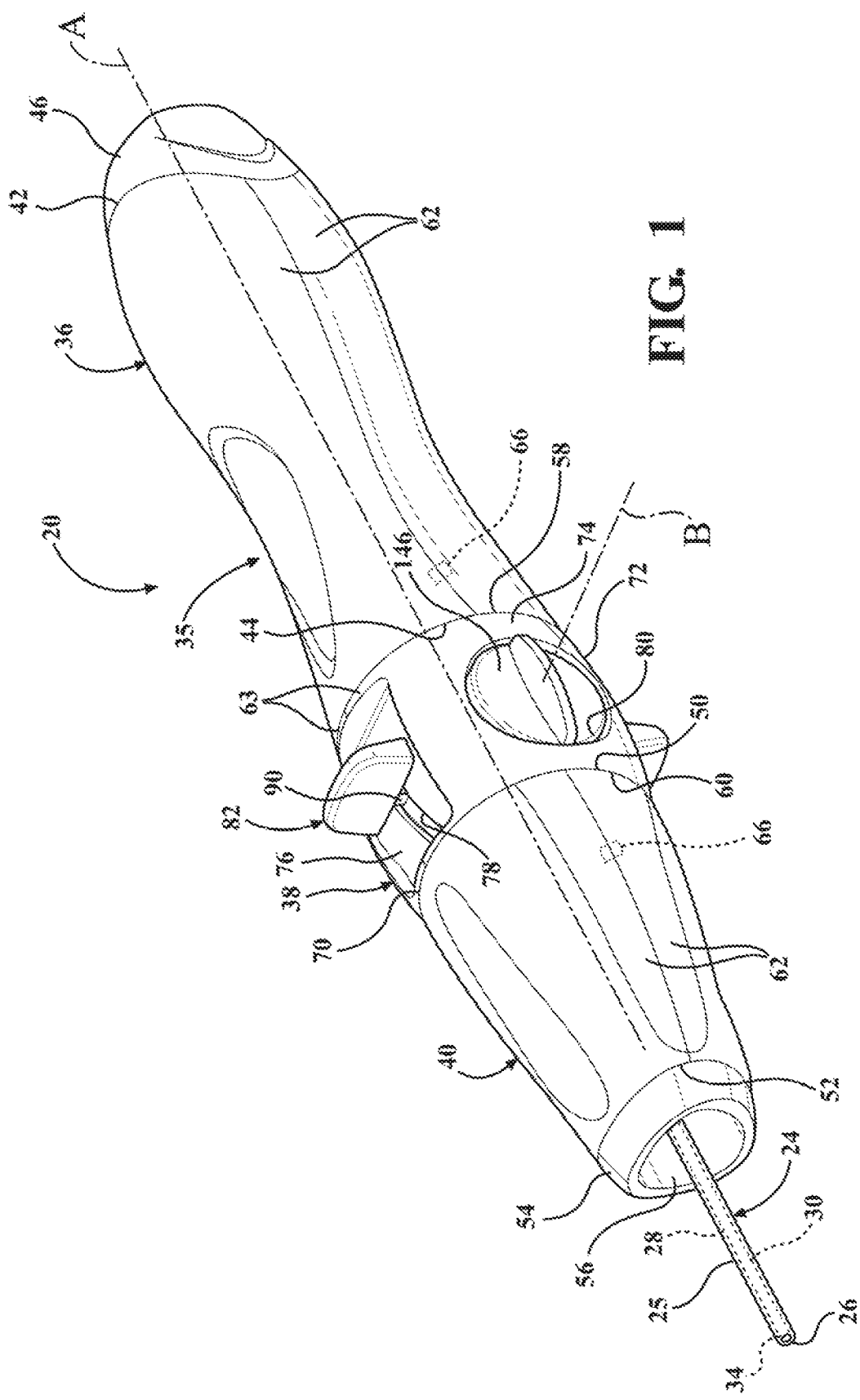
FIG. 1 is a perspective view of an example embodiment of a modular handle assembly.

Referring to the Figures, wherein like numerals indicate corresponding parts throughout the several views, a modular handle assembly 20 for a steerable catheter 24 is generally shown. With reference to FIG. 1, the catheter 24 has a tubular and flexible elongated body 25 that extends to a distal tip 26. A first deflection wire 28 and a second deflection wire 30 each extend between a proximal end 32 (shown in FIGS. 2-3) and a distal end 34 (shown in FIG. 1). The distal ends 34 are connected to the distal tip 26 of the catheter 24 and extend through the body 25 for curling the distal tip 26 in response to movement of the first and second deflection wires 28, 30. It should be appreciated that alternatively, a single deflection wire could be utilized.

With continued reference to FIG. 1, the modular handle assembly 20 further includes a handle 35 that has a rear handle segment 36, a control housing segment 38, and a front handle segment 40 positioned in end-to-end relationship with one another from a rear end of the rear handle segment 36 to a forward end 52 of the front handle segment 40.

The rear handle segment 36 generally has a tube shape and extends along a longitudinal axis A from the rear end 42 to a front end 44. A rear cap 46 is connected to the rear end 42 of the rear handle segment 36. Similarly, the front handle segment 40 generally has a tube shape and extends along the longitudinal axis A from a back end 50 to the forward end 52. The front handle segment 40 is disposed about the steerable catheter 24. A front cap 54 is coupled with the forward end 52 of the front handle segment 40 and defines an opening 56 along the longitudinal axis A. The front cap 54 terminates at a terminal end that is arc-shaped in cross-section such that it functions as a strain relief for the elongated body 25 of the catheter 24. Specifically, because of the radius of curvature of the end of the front cap 54, the elongated body 25 is unable to sharply bend about the front cap 54, and thus deformation of the deflection wires 28, 30 is prevented.

The control housing segment 38 is positioned axially between the front end 44 of the rear handle segment 36 and the back end 50 of the front handle segment 40. The control housing segment 38 generally has a tube shape and extends along the longitudinal axis A between a first end 58 coupled with the front end 44 of the rear handle and a second end 60 coupled with the back end 50 of the front handle segment 40.

The rear and front handle segments 36, 40 are each comprised of a pair of halves 62 that are mirror images of one another along a plane that extends diametrically through rear and front handle segments 36, 40 through the longitudinal axis A. Likewise, the control handle segment 38 is comprised of a pair of halves 63 that are a mirror image of one another along a plane that extends diametrically through the control housing segment 38 through the longitudinal axis A. A plurality of mechanical attachments 66 (schematically shown) removeably attach the halves 62, 63 of the rear handle, front handle and control housing segments 36, 40, 38 to one another. The mechanical attachments 66 may include, but are not limited to, slots and tabs. Furthermore, one or more ribs (not shown) may extend from an inside surface of each of the halves 62, 63 of the rear handle, front handle and control housing segments 36, 40, 38 for providing structural rigidity to the rear handle, front handle and control housing segments 36, 40, 38.

The control housing segment 38 defines a top region 70 and bottom region 72 opposite one another, and a pair of side regions 74 opposite one another and between the top and bottom regions 70, 72. The top and bottom regions 70, 72 each define an arcuate guide face 76 and a pivot opening 78 that has a generally rectangular shape. Furthermore, one of the side regions 74 defines a generally circular shaped rotary opening 80.

Figure 4:
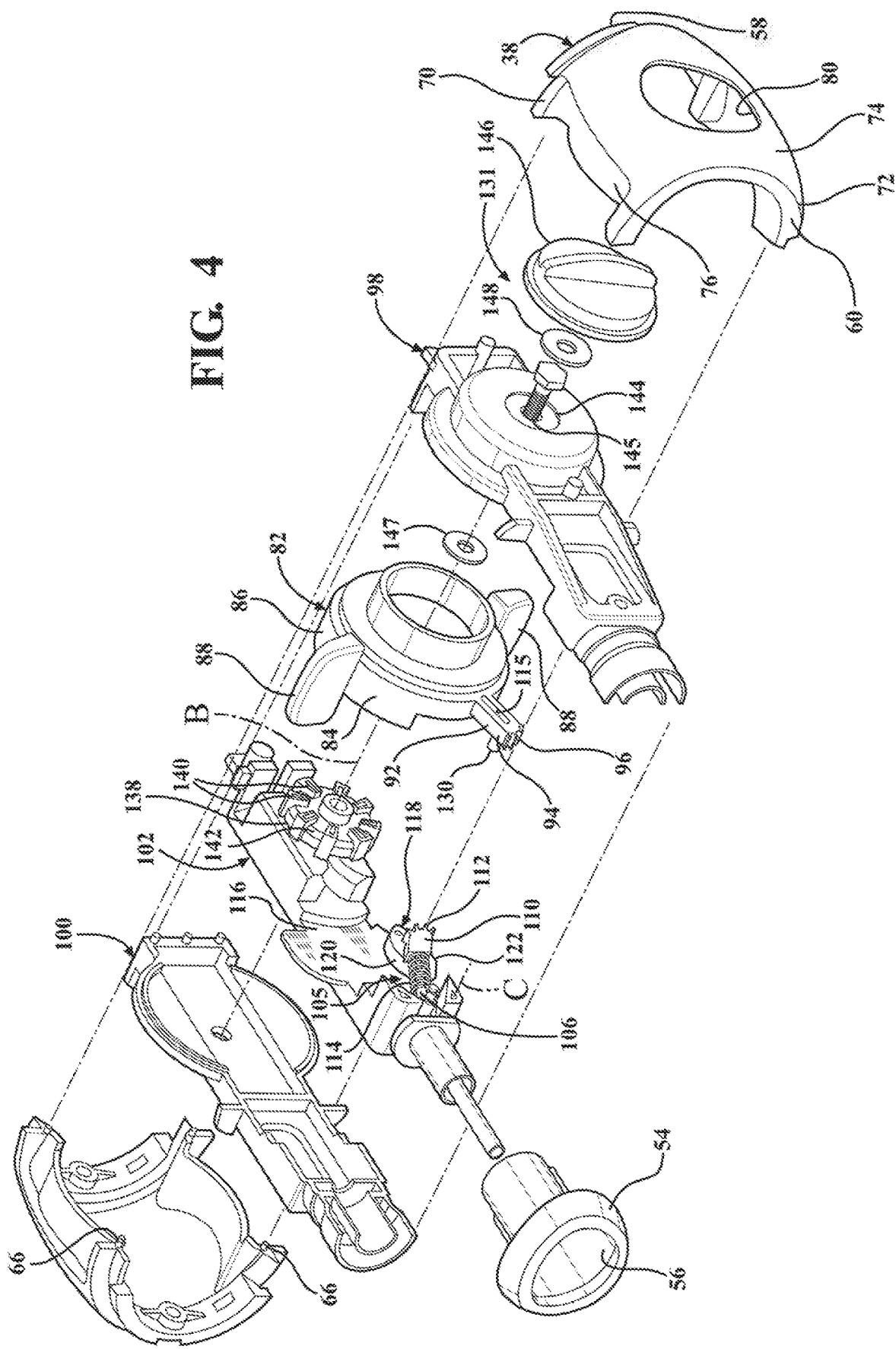
FIG. 4 is a perspective exploded view of a support housing segment and components contained therein of the modular handle assembly.

As best shown in FIG. 4, a dial 82 is disposed in the control housing segment 38 along a first rotary axis B extending perpendicularly through the longitudinal axis A. The dial 82 has a generally ring-shaped band portion 84 that presents an outer circumference 86. A pair of paddles 88 are connected to the outer circumference 86 of the band portion 84 on circumferentially opposite sides of the dial 82 with a leg 90. The leg 90 of each of the paddles 88 extends through one of the pivot openings 78, and the paddles 88 are each slideably disposed against one of the arcuate guide faces 76 of the top and bottom regions 70, 72 of the control housing segment 38 for guiding the paddles 88 during rotation thereof. A first gear arm 92 extends radially from the outer circumference 86 of the band portion 84 relative to the first rotary axis B and circumferentially between the paddles 88. The first gear arm 92 terminates at a first gear tip 94 that presents a first friction surface 96.

Figure 2:
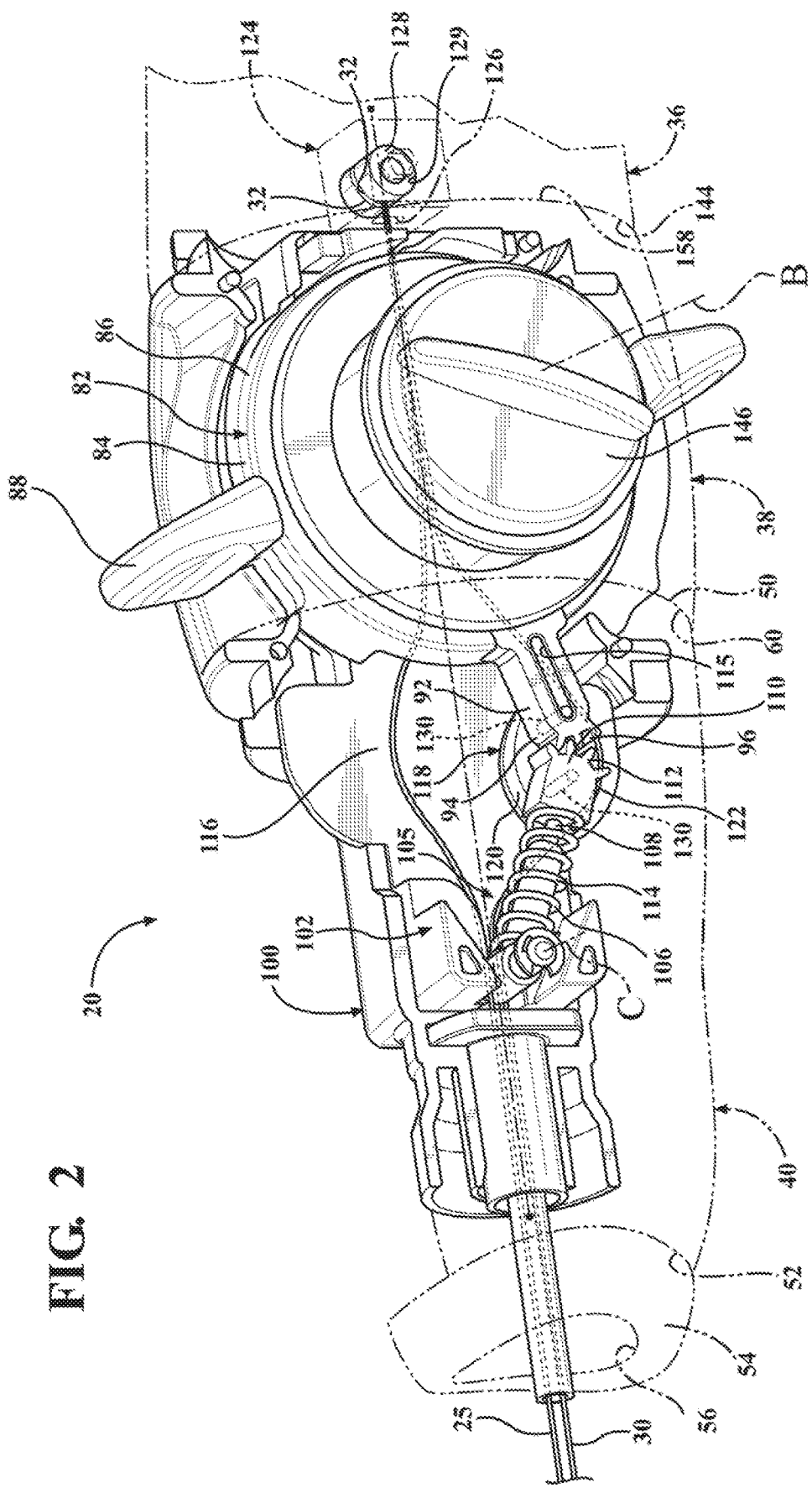
FIG. 2 is a side perspective view of a dial, first gear arm and second gear arm of the modular handle assembly in a first rotational position.
Figure 3:
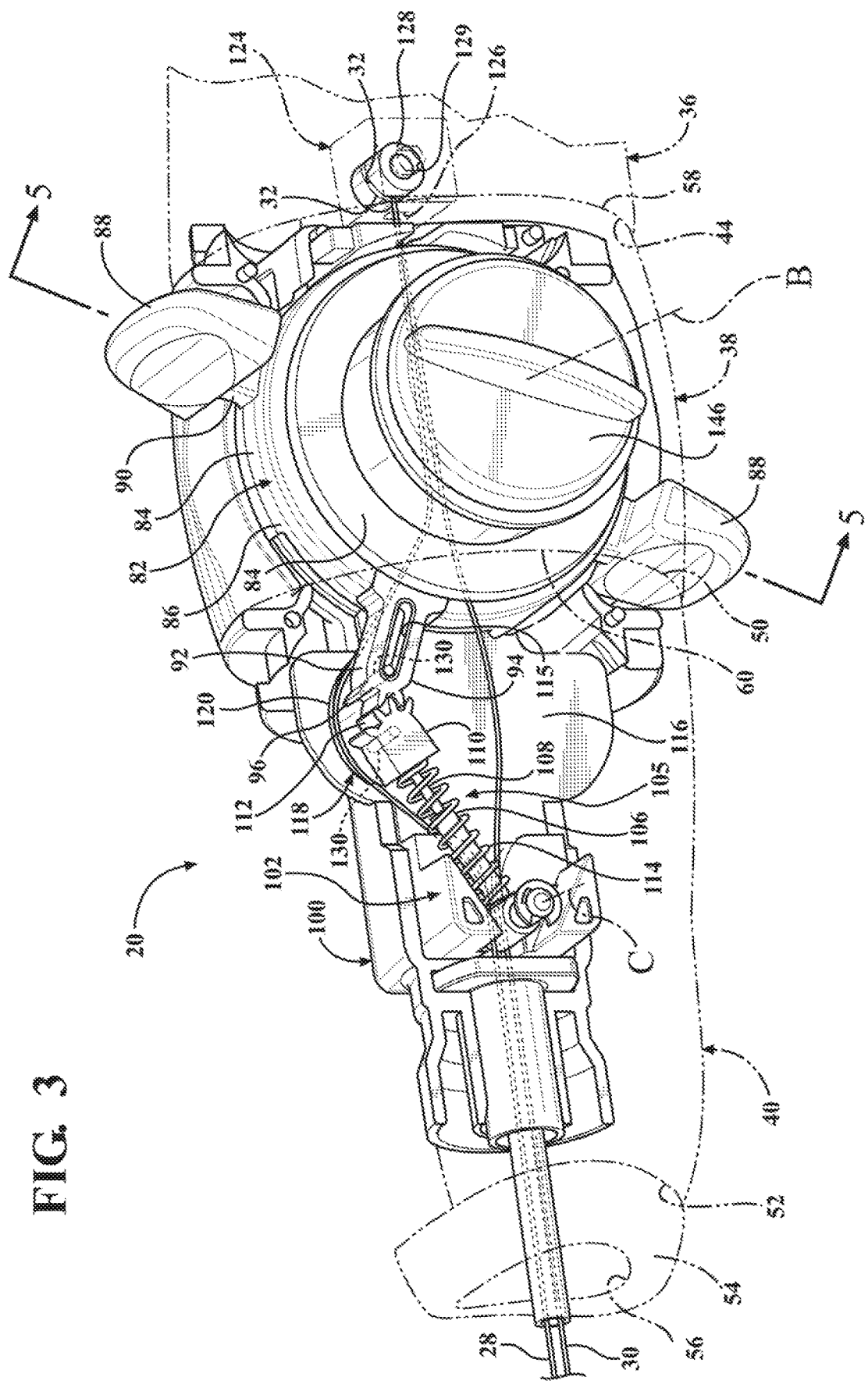
FIG. 3 is a side perspective view of a dial, first gear arm and second gear arm of the modular handle assembly in a second rotational position.

A first dial support 98 and a second dial support 100 are positioned in the control housing segment 38 and the front handle segment 40 on opposite sides of the dial 82 relative to the first rotary axis B. The first dial support 98 rotatably supports the dial 82 along the first rotary axis B. A central support member 102 extends along the longitudinal axis A between the dial 82 and the second dial support 100. As best presented in FIGS. 2-3, a second gear arm 105 is rotatably connected to the central support member 102 in the front handle segment 40 along a second rotary axis C that is parallel to the first rotary axis B. The second gear arm 105 includes an outer tube 106 and an inner rod 108 telescopingly received by the outer tube 106. The inner rod 108 terminates at a second gear tip 110 that presents a second friction surface 112. A spring 114 is positioned about the second gear arm 105 and biases the second gear tip 110 toward the first gear tip 94. The second friction surface 112 is disposed against the first friction surface 96 such that rotation of the dial 82 with the paddles 88 in a first rotary direction about the first rotary axis B causes rotation of the second gear arm 105 in an opposite direction about the second rotary axis C. For example, FIG. 2 illustrates the first and second gear arms 102, 105 disposed in a first position and FIG. 3 illustrates the first and second gear arms 102, 105 rotated into a second position. The arrangement of the telescoping outer tube 106 and inner rod 105 and spring 114 allows the first and second gear arms 92, 105 to rotate relative to one another, each from a respective fixed pivot point because the second gear arm 105 telescopingly shortens as the first and second gear tips 94, 110 rotate about the first rotary axis B. The spring 114 also serves the function of providing an increasing compressive load as the first and second gear tips 94, 110 approach alignment with the longitudinal axis A. This results in an additional actuation force to assist the user in deflecting the wire 30. It should be appreciated that various springs with different spring constants may be utilized to provide a desired actuation force.

In the example embodiment, the first friction surface 96 includes a plurality of first teeth 96, the second friction surface 112 is a plurality of second teeth 112, and the first and second gear teeth 96, 112 are in meshed relationship with one another. It should be appreciated that other friction surfaces 112, 96 could be utilized.

In the example embodiment, the central support member 102 presents a sliding surface 116 that is positioned between the first and second rotary axes B, C. The sliding surface 116 is planar and extends along a plane that extends through the first and second rotary axes B, C and is perpendicular to the longitudinal, first and second rotary axes A, B, C.

As best shown in FIG. 2-3, a cam 118 is coupled with at least one of the first and second gear tips 94, 110. The cam 118 is slideable along the sliding surface 116 during movement of the first and second gear tips 94, 110. The cam 118 has an arc-shaped upper deflection surface 120 and an arc-shaped lower deflection surface 122 opposite the upper deflection surface 120. The upper and lower deflection surfaces 120, 122 protrude in opposite directions from one another.

A tuning block 124 is connected to the first end 58 of the control housing segment 38 in the rear handle segment 36 of the handle 35. The tuning block 124 includes a passage 126 that receives the proximal ends 32 of the first and second deflection wires 28, 30. A cylinder 128 is rotatably received in an orifice 129 of the tuning block 124. The proximal ends 32 of the first and second deflection wires 28, 30 are wrapped about the cylinder 128 of the tuning block 124. The first and second deflection wires 28, 30 are tightenable in response to rotation of the cylinders 128. Accordingly, the first and second deflection wires 28, 30 terminate and are fixed to the same tuning block 124, and the tuning block 124 can be tensioned after assembly to adjust the amount of pre-load on the first and second deflection wires 28, 30 to ensure that there is no slack. It should be appreciated that the first and second deflection wires 28, 30 may be conditioned by being deflected several times to pre-stretch the same. This tensioning allows the pre-load to be adjusted.

The first deflection wire 28 extends from the tuning block 124 and about the upper deflection surface 120 of the cam 118 and out of the opening 56 of the front handle portion 36. Similarly, the second deflection wire 30 extends from the tuning block 124 and about the lower face of the cam 118 and out of the opening 56 of the front cap 54. During rotation of the dial 82, the upper deflection surface 120 of the cam 118 deflects the first deflection wire 28 due to corresponding movement of the cam 118. Likewise, the lower deflection surface 122 of the cam 118 deflects the second deflection wire 30 due to corresponding movement of the cam 118. Each deflection wire 28, 30 is deflected independently based on the direction of rotation of the dial 82. The deflection of the first and second deflection wires 28, 30 steers the distal end 34 of the steerable catheter 24. A pair of pivot pins 130 each pivotably connect the cam 118 with one of the first and second gear tips 94, 110 such that the cam 118 remains in the same horizontal orientation during pivoting of the first and second gear arms 92, 104. A slot 115 is defined in the first gear arm 92 for allowing the cam 118 to slide relative to the first gear arm 92 during pivoting of the first and second gear arms 92, 104. It should be appreciated that due to this arrangement, the subject handle assembly 20 does not have to utilize deflectable wires that transition from a metal to a polymer fiber as is commonly used with steerable catheters, because the deflection wires 28, 30 do not have to be rotated about a barrel during adjustment of the catheter 24. Furthermore, it should be appreciated that the radius of the upper and lower deflection surfaces 120, 122 and the ability of the cam 118 to remain in a horizontal position during pivoting of the first and second gear arms 92, 104 prevent overbending of the deflection wires 28, 30, thus preventing damage to the deflection wires 28, 30.

Figure 5:
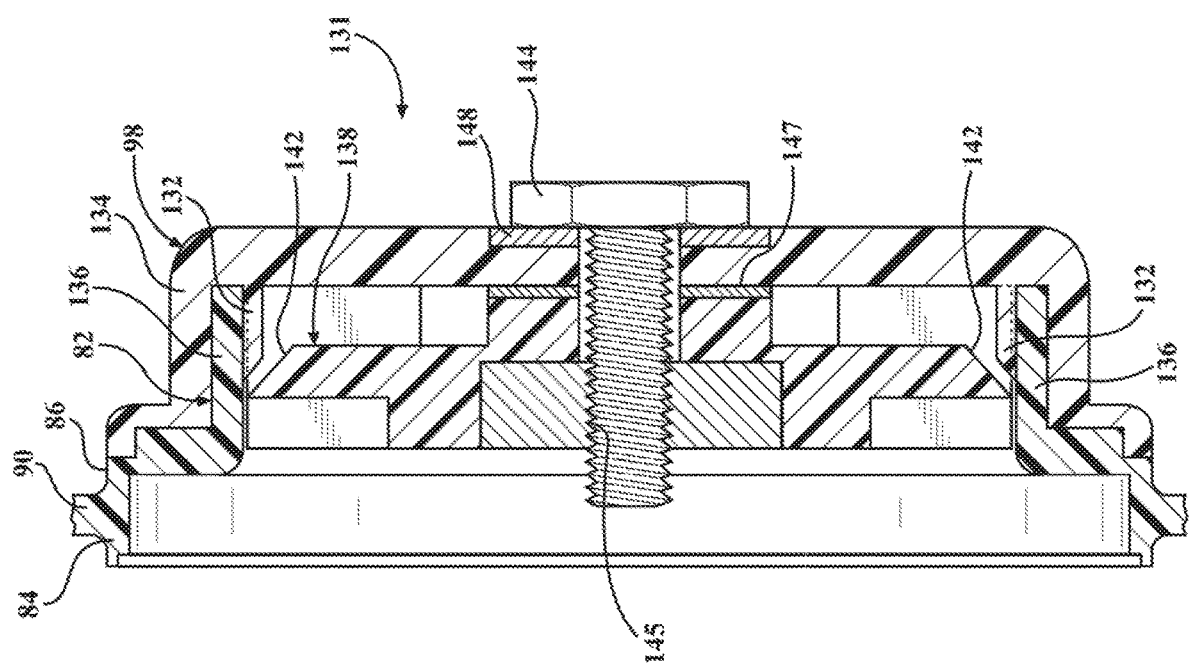
FIG. 5 is a side cross-sectional view of a brake assembly of the modular handle assembly.
Figure 6:
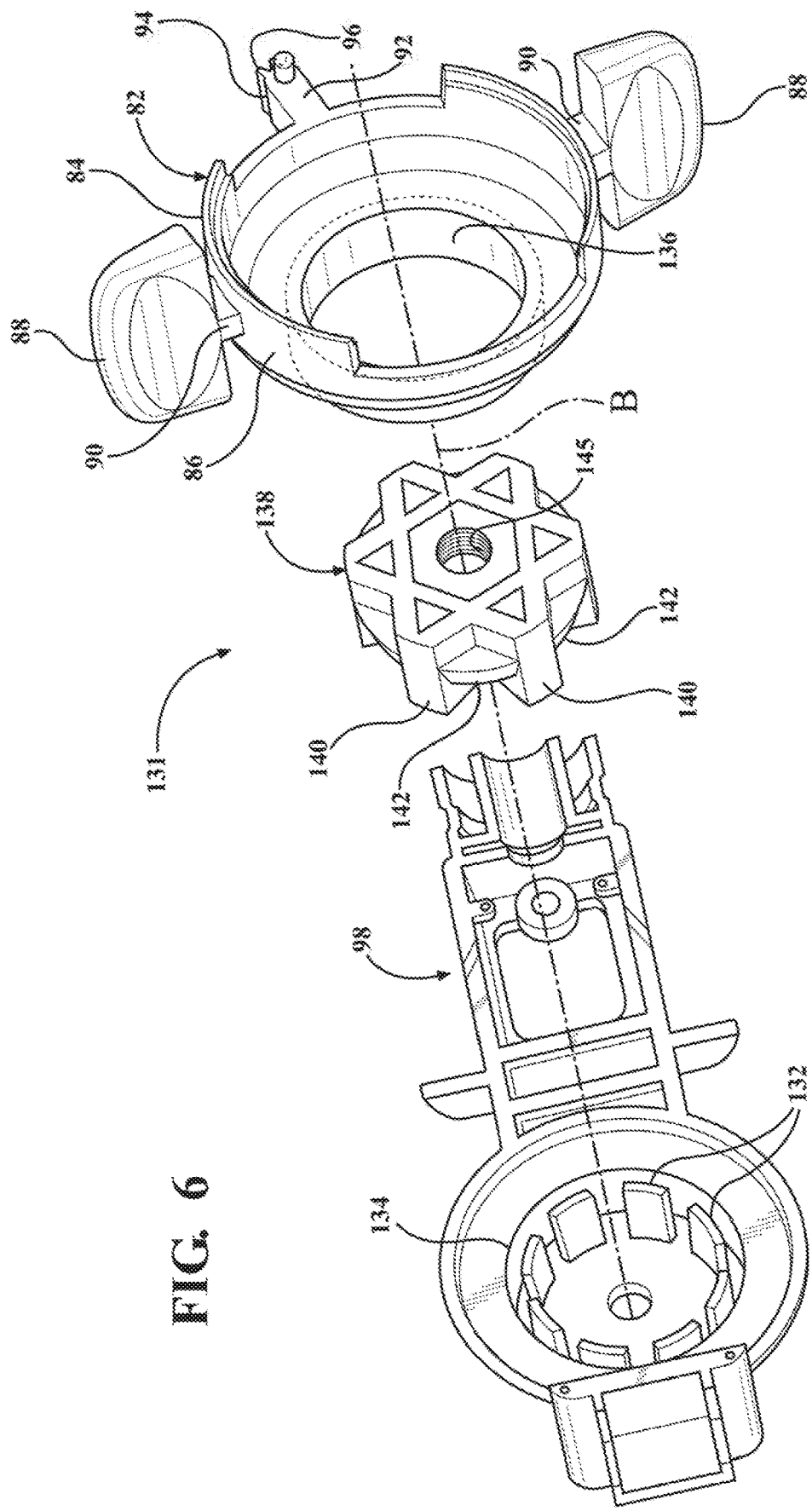
FIG. 6 is a perspective exploded view of the brake assembly of the modular handle assembly.

As best shown in FIGS. 5 and 6, a brake assembly 131 is connected to the first dial support 98 in the control housing segment 40 and coupled with the dial 82 for selectively inhibiting rotation of the dial 82 about the first rotary axis B to inhibit axial movement of the first and second deflector wires 28, 30. In other words, the brake assembly 131 is utilized to increase or decrease the amount of force required to rotate the dial 82 and hold it in a desired position by the user. The brake assembly 131 includes a plurality of fingers 132 that extend from the first dial support 98 in the control handle 40. The fingers 132 extend generally parallel to the first rotary axis B and annularly about the first rotary axis B in circumferentially spaced relationship with one another. Each of the fingers 132 tapers inwardly as the finger 132 extends from the first dial support 98. The brake assembly 131 further includes a first annular rim 134 that extends from the first dial support 98 continuously annularly about the plurality of fingers 132. The dial 82 also includes a second annular rim 136 that extends from the dial 82 and is sandwiched radially between the plurality of fingers 132 and the first annular rim 134. The brake assembly 131 further includes a drum 138 positioned radially inward of the plurality of fingers 132. The drum 138 is moveable along the first rotary axis B. The drum 138 generally has a disc shape and includes a plurality of second fingers 140 extending from the drum 138 in parallel relationship with the first rotary axis B and positioned annularly about the drum 138 and circumferentially spaced from one another. The second fingers 140 are interleaved with the first fingers 132.

The drum 138 further includes a plurality of tapered surfaces 142 that are circumferentially aligned with the first fingers 132 and axially aligned relative to the first rotary axis B with the first fingers 132 such that axial movement of the drum 138 toward the dial 82 support causes radial outward movement of the first fingers 132 against the second annular flange of the dial 136 to inhibit rotation of the dial 82. A bolt 144 extends along the first rotary axis B through the first dial support 98. The bolt 144 is threadedly connected to the drum 138 in a threaded bolt passage 145 along the first rotary axis B for causing axial movement of the drum 138 in response to tightening of the bolt 144. As best shown in FIGS. 1-4, a tightening handle 146 is connected to the bolt 144 in the rotary opening 80 of the support housing for allowing a user to tighten the bolt 144. With reference back to FIGS. 5-6, a first washer 147 is positioned about the bolt 144 and between the first dial support 98 and the drum 138. A second washer 148 is positioned about the bolt 144 and between the first dial support 98 and the tightening handle 146.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular handle assembly comprising:
   a steerable catheter having at least one deflection wire;
   a handle extending along a longitudinal axis for being positioned about a portion of the steerable catheter;
   a dial rotatably connected to said handle and rotatable about a first rotary axis extending transverse to said longitudinal axis;
   a first gear arm extending radially relative to said first rotational axis from said dial and terminating at a first gear tip presenting a first friction surface;
   a second gear arm rotatably connected to said handle and rotatable about a second rotary axis extending in spaced and parallel relationship with said first rotary axis;
   said second gear arm extending radially relative to said second rotary axis and terminating at a second gear tip presenting a second friction surface disposed against said first friction surface such that rotation of said dial in a first rotary direction about said first rotary axis effectuates rotation of said second gear arm in an opposite direction about said second rotary axis; and
   a cam coupled with at least one said first and second gear tips for providing movement of said cam during rotation of said dial, said cam presenting at least one deflection surface for deflecting said at least one deflection wire extending across said at least one deflection surface during rotation of said dial to steer a distal end of said steerable catheter with said first and second gear tips.

2. The modular handle assembly as set forth in claim 1 wherein said cam is rotatably coupled with said at least one of said first and second gear tips.

3. The modular handle assembly as set forth in claim 2 wherein at least one pivot pin rotatably couples said cam with said at least one of said first and second gear tips.

4. The modular handle assembly as set forth in claim 3 wherein said cam is rotatably coupled with both of said first and second gear tips, and said at least one pivot pin includes a pair of pivot pins each rotatably coupling said cam and one of said first and second gear tips to cause said cam to maintain a horizontal position during movement of said first and second gear tips.

5. The modular handle assembly as set forth in claim 3 wherein said one of said first and second gear arms defines a slot receiving one of said pivot pins for allowing said cam to slide relative to said one of said first and second gear arms.

6. The modular handle assembly as set forth in claim 1 wherein said at least one deflection wire includes a first deflection wire and a second deflection wire, and wherein said at least one deflection surface of said cam includes an upper deflection surface for deflecting said first deflection wire extending across said upper deflection surface and a lower deflection surface for deflecting said second deflection wire extending across said lower deflection surface during rotation of said dial.

7. The modular handle assembly as set forth in claim 1 wherein said upper and lower deflection surfaces of said cam each have an arcuate shape, and wherein said upper and lower deflection surfaces protrude in opposite directions from one another to prevent over bending of said at least one deflection wire during rotation of said pivot pins.

8. The modular handle assembly as set forth in claim 1 wherein said first friction surface of said first gear tip includes a plurality of first teeth, wherein said second friction surface of said second gear tip includes a plurality of second teeth and wherein said first and second teeth are disposed in meshed relationship with one another.

9. The modular handle assembly as set forth in claim 1 wherein said second gear arm includes an outer tube and an inner rod telescopingly received by said outer tube, and wherein said inner rod terminates at said second gear tip to allow said second gear arm to shorten and lengthen during pivoting of said second gear arm about said second rotary axis.

10. The modular handle assembly as set forth in claim 9 further comprising a biasing member biasing said second gear tip toward said first gear tip to provide a compressive force against the second gear tip to provide an actuation force to assist a user in deflecting said at least one deflection wire.

11. The modular handle assembly as set forth in claim 9 wherein said biasing member is a spring positioned about said first and second arms.

12. The modular handle assembly as set forth in claim 1 further comprising a tuning block fixed inside said handle for securing a proximal end of said at least one deflection wire relative to said handle.

13. The modular handle assembly as set forth in claim 12 wherein said tuning block defines a passage for receiving the proximal end of said at least one deflection wire, an orifice extending into said passage, and a spindle received by said orifice for winding said at least one deflection wire to tighten said at least one deflection wire.

14. The modular handle assembly as set forth in claim 1 further comprising a brake assembly coupled with the dial for selectively inhibiting rotation of the dial about the first rotary axis to inhibit axial movement of said at least one deflection wire.

15. The modular handle assembly as set forth in claim 14 further comprising a knob rotatably connected to said brake assembly for allowing a user to selectively inhibit axial movement of said at least one deflection wire.

16. The modular handle assembly as set forth in claim 14 wherein said brake assembly includes a first dial support fixed relative to said housing, at least one first finger extending parallel to said first rotary axis from said first dial support, a first rim extending parallel to said first rotary axis from said first dial support in radially spaced relationship with said at least one first finger, said dial includes a second rim positioned radially between said at least one first finger and said first rim, a drum moveable along said first rotary axis and rotatably fixed relative to said dial support, wherein said drum includes at least one engagement surface in alignment with said at least one first finger relative to said first rotary axis, and wherein at least one of said at least one first finger and said at least one engagement surface is tapered such that axial movement of said drum relative to said first dial support causes said at least one first finger to be radially pressed against said second rim of said dial and causes said second rim of said dial to be radially pressed against said first rim of said first dial support for inhibiting rotation of said dial about said first rotary axis.

17. The modular handle assembly as set forth in claim 16 wherein said at least one first finger includes a plurality of first fingers positioned in circumferentially spaced relationship with one another about said first rotary axis, and wherein said at least one engagement surface of said drum includes a plurality of engagement surfaces in circumferentially spaced relationship relative to one another about said first rotary axis and each in alignment with one of said first fingers relative to said first rotary axis.

18. The modular handle assembly as set forth in claim 17 wherein said drum includes a plurality of second fingers each positioned circumferentially between two of said engagement surfaces, and wherein said second fingers are interleaved with said first fingers of said first dial support.

19. The modular handle assembly as set forth in claim 16 further including a bolt extending along said first rotary axis through said first dial support and threadedly connected to said drum for causing axial movement of said drum in response to tightening of said bolt.

20. The modular handle assembly as set forth in claim 1 wherein said dial has an outer circumference and presents at least one paddle connected to said outer circumference for allowing said dial to be rotated by a user.

* * * * *